United States Patent
Seddon et al.

(10) Patent No.: US 6,774,240 B2
(45) Date of Patent: Aug. 10, 2004

(54) PROCESS FOR PREPARING AMBIENT TEMPERATURE IONIC LIQUIDS

(75) Inventors: Kenneth R. Seddon, Donaghadee (GB); Adrian J Carmichael, Coventry (GB); Martyn J. Earle, Belfast (GB)

(73) Assignee: The Queen's University of Belfast, Belfast (GB)

( * ) Notice: Subject to any disclaimer, the term of this patent is extended or adjusted under 35 U.S.C. 154(b) by 0 days.

(21) Appl. No.: 10/148,406

(22) PCT Filed: Dec. 1, 2000

(86) PCT No.: PCT/GB00/04584

§ 371 (c)(1),
(2), (4) Date: Sep. 9, 2002

(87) PCT Pub. No.: WO01/40146

PCT Pub. Date: Jun. 7, 2001

(65) Prior Publication Data

US 2003/0080312 A1 May 1, 2003

(30) Foreign Application Priority Data

Dec. 1, 1999 (GB) ............................................. 9928290

(51) Int. Cl.[7] ...................... C07D 233/06; C07D 211/80
(52) U.S. Cl. .................................... 548/347.1; 546/348
(58) Field of Search ....................... 548/347.1; 546/348

(56) References Cited

U.S. PATENT DOCUMENTS 6,372,829 B1 * 4/2002 Lamanna et al. ............. 524/99

FOREIGN PATENT DOCUMENTS

WO PCT/GB95/00252 8/1995

OTHER PUBLICATIONS

Bonhote et al., 1997, "Hydrophobic, highly conductive ambient–temperature molten salts", CAS:128:101789.*
Howarth, et al., Moisture Stable Dialkylimidazolium Salts as Heterogeneous and Homogeneous Lewis Acids in the Diels–Alder Reaction; *Tetrahedron Letters,* vol. 38, No. 17, pp. 3097–3100.

* cited by examiner

*Primary Examiner*—Rita Desai
*Assistant Examiner*—Robert Shiao
(74) *Attorney, Agent, or Firm*—Hodgson Russ LLP

(57) ABSTRACT

A process for preparing an ionic liquid or salt, formed by reaction between an organic base and an alkylating agent, wherein the alkylating agent is a fluorinated ester or an alkyl sulfonate, is described. Suitable organic bases include imidazoles, substituted imidazoles, pyridines and substituted pyridines. The so-formed products can be subsequently transformed into different ionic liquids or salts by metathesis.

14 Claims, No Drawings

PROCESS FOR PREPARING AMBIENT TEMPERATURE IONIC LIQUIDS

This invention relates to a process for processing ambient temperature ionic liquids.

Ambient temperature ionic liquids based upon the 1,3-dialkylimidazolium cation were first reported in 1982 by Wilkes et al[1]. These systems were based upon the chloroaluminate anion and although they possess many useful properties (e.g. wide liquids, thermal stability and large electrochemical window) they are reactive to certain materials and are sensitive to moisture. An air and water stable system was developed by Wilkes and Zaworotko in 1992 based upon the tetrafluoroborate anion[2]. Since this report a wide range of ionic liquids containing different anions have appeared in the literature[3]. These systems have received much attention and recent studies have shown that ambient temperature ionic liquids can be used as solvents for a range of chemical reactions including polymerisation[4], hydrogenation[5], Friedel-Crafts acylations[6] and for the Diels-Alder reaction[7].

The principal route currently employed in the synthesis of the air and moisture stable 1,3-dialkylimidazolium ionic liquids is outlined in Scheme 1.

Scheme 1

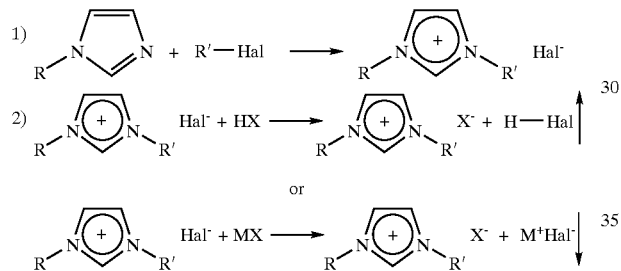

The first step with this method is the alkylation of 1-alkylimidazole with a haloalkane to give a 1,3-dialkylimidazolium halide salt. The second step is metathesis of the halide for the appropriate anion. The second step can be carried out with either an acid or a metal salt to eliminate H-Hal as or precipitate M⁺Hal respectively. It is here that the intrinsically good solvating properties of these ionic liquids become a problem. In many of the syntheses the ionic liquids solvate the halide waste so effectively that complete removal is not effected. Halide contamination of the ionic liquids is a problem that must be overcome for them to be used as reaction solvents on a large scale. For instance, when used as media for transition metal catalysed reactions the presence of strongly co-ordinating halide ions have been shown to reduce catalyst activity[5]. The opportunity exists in many reactions for the residual halides to be oxidised to halogens which will result with many substrates and can corrode apparatus. In addition, this method always generates a stoicheiometric amount of halide salt as a waste product. When metathesis is carried out using a silver salt the route becomes prohibitively expensive upon scale up. Employing the alkali metal salts reduces the cost, but not the waste.

We have developed a new method for the synthesis of the air- and moisture-stable ionic liquids that overcomes the possibility of halide impurities and reduces the amount of waste products. This method is based upon the use of fluorinated esters or alkyl sulfonates as replacements for haloalkanes.

Thus, according to one aspect of the present invention, there is provided a process for preparing an ionic liquid or salt formed by reaction between an organic base and an alkylating agent, wherein the alkylating agent is a fluorinated ester or an alkyl sulfonate.

The so-formed product of the organic base and ester or sulfonate could subsequently be transformed into a different ionic liquid or salt with a range of different anions by metathesis, preferably using an acid or metal salt.

In one embodiment of the present invention, the cation formed is an N-alkylated base.

For this, the organic base could be an imidazole or a substituted imidazole. Preferably, the substituted imidazolium salt is a 1,3-dialkylimidazolium trifluoroethanoate and the (n−1)-substituted imidazole is a 1-alkylimidazole.

Alternatively, the organic base is a pyridine or a substituted pyridine.

Other organic bases include the phosphines and sulfides.

Also preferably a co-solvent is used.

The following description will focus on using the organic base 1-methylimidazole, the imidazole most commonly used in the preparation of ambient temperature ionic liquids, and ethyl trifluoroethanoate as the alkylating agent.

The synthesis is similar to that mentioned above in Scheme 1, in that there is an alkylation and a metathesis step to give the desired ionic liquid as shown in Scheme 2.

Scheme 2

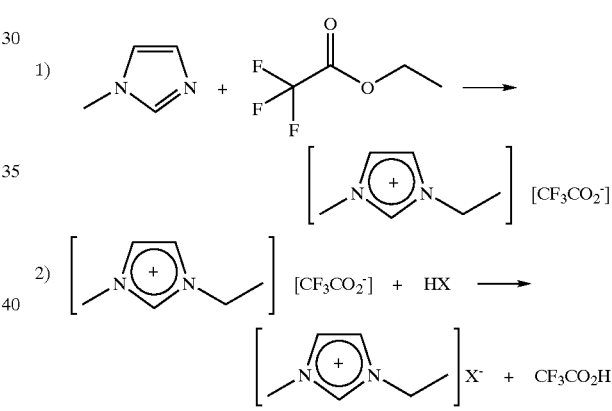

The reaction of 1-methylimidazole with ethyl trifluoroethanoate to give 1-ethyl-3-methylimidazolium trifluoroethanoate, [emim] [TFA], proceeds cleanly and smoothly at moderate temperature (70° C.). However, some reduction in the rate of reaction may occur as the reaction proceeds. The primary reason for the reduction in rate is that unreacted 1-methylimidazole concentrates in the ionic liquid phase as it forms, while the ethyl trifluoroethanoate is only slightly soluble in [emim] [TFA]; thus reactants are kept apart Addition of a co-solvent to solubilise reactants and products, for example acetonitrile, overcomes this problem and a significant rate enhancement is observed. Alternatively, the reaction may be performed in an autoclave.

[emim] [TFA] is an ambient temperature ionic liquid with all the expected characteristics in its own right. In addition, it is a good starting point for the synthesis of other air- and moisture-stable ionic liquids with metathesis of the trifluoroethanoate anion easily achieved. Addition of the desired acid to [emim] [TFA] yields a reaction mixture with only one volatile material, trifluoroethanoic acid (b.pt.72° C.), which is easily removed under vacuum. This is true as long as the added acid is of higher boiling point than $CF_3CO_2H$, which most acids of interest are (e.g. $HPF_6$, $HBF_4$, $H_3PM_{12}O_{40}$ (M=W, Mo), $H_3PO_4$). This gives the desired ionic liquid, without extractions and washings, in a halide free state.

The use of longer alkyl chain esters (e.g. hexyl trifluoroethanoate) works equally as well with 1-alkylimidazoles to give the desired product. The use of more fluorinated esters (e.g. ethyl heptafluorobutanoate) is still possible although they may have the drawback of generating a less volatile carboxylic acid by-product.

Alkyl sulfonates for use as the alkylating agent are also well known in the art, such as a methyl sulfonate; more particularly butyl methylsulfonate.

According to a second aspect of the present invention there is provided a process for preparing an ionic liquid or salt formed by reaction between an organic base and fluorinated alkylating agent whenever the so-formed fluorinated by-product has a lower boiling point than the acid added to the alkylating agent.

The cation formed is preferably an N-alkylated base. This is a general method that can be used to synthesise a range of (imidazolium, possibly substituted imidazolium) ionic liquids and low melting point salts.

The present invention extends to any product obtainable from any of the new processes herein described. Particularly, it extends to a 1,3-dialkylimidazolium-based ionic liquid whenever prepared by reacting 1-alkylimidazole with a fluorinated ester, followed by metathesis.

The present invention also extends to the use of any ester able to act in a similar manner to form an ambient temperature ionic liquid with an organic base.

The reaction conditions required to effect the processes of the present invention will be known or calculable to those skilled in the art.

The use of fluorinated compounds, although expensive, is desired for two reasons. Firstly, fluorination of the ester activates the molecule for the alkylation step, and secondly, fluorinated products are more volatile and of lower boiling point than their non-fluorinated analogues, thus making separation of the ionic liquid easier. The cost of using fluorinated esters should not be prohibitively expensive as the carboxylic acid by-product can be recycled. An overall process is envisaged as shown in Scheme 3.

Scheme 3

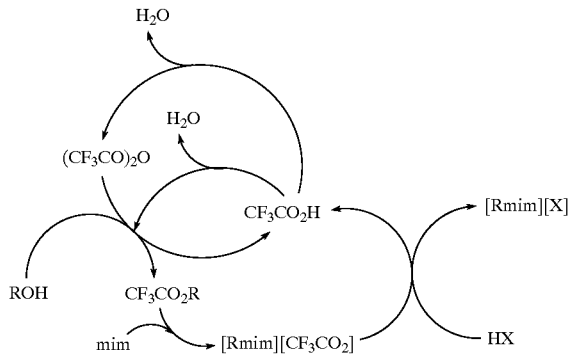

R=hydrocarbyl, or substituted hydrocarbyl.
X=any anion such as nitrate, tetrafluoroborate, hexafluorophosphate, etc.
mim=1-methylimidazole.
R and X are used in their normal context as is well known in the art.

As scheme 3 shows, the waste trifluoroethanoic acid is recovered and converted into the reactive ester either through a straight esterification or via the anhydride. This gives the following balanced equation for the synthesis of ambient temperature ionic liquids;

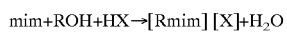

The present invention thus provides a new synthetic route to ambient temperature ionic liquids that ensures the product is halide-free. If the metathesis is performed with an acid rather than a metal salt, then the product will be both halide-free and metal-free. In addition, the alkylating agent can be regenerated from inexpensive and readily available materials, thus reducing waste.

EXPERIMENTAL

Preparation of 1-ethyl-3-methylimidazolium trifluoroethanoate, [emim] [TFA].

1-Methylimidazole (2.5 g, 30.4 mmol) and ethyl trifluoroethanoate (25.8 g, 181.6 mmol) were dissolved in ethanenitrile (20 cm$^3$). The resultant solution was placed in a sealed glass vessel and stirred at 70° C. for 5 days giving a pale yellow solution. The volatiles were removed in vacuo giving [emim] [TFA] in 100% yield.

Preparation of 1-ethyl-3-methylimidazolium tetrafluoroborate, [emim] [BF$_4$]

To [emim] [TFA] (1.0 g, 4.5 mmol) was added one equivalent of fluoroboric acid (0.412 cm$^3$ of 10.8M aq. solution, 4.5 mmol) and the mixture was stirred overnight at room temperature. Heating under vacuum at 100° C. removes trifluoroethanoic acid and water giving [emim] [BF$_4$].

Preparation of 1-ethyl-3-methylimidazolium hexafluorophosphate, [emim] [PF$_6$]

To [emim] [TFA] (2.0 g, 8.9 mmol) dissolved in water (10 cm$^3$) was added hexafluorophosphoric acid (2 cm$^3$ of 6.79M aq. solution, 13.58 mmol). This gave [emim] [PF$_6$] as a white precipitate which was collected by vacuum filtration.

Preparation of butyl methanesulfonate (BuOMs)

To a 500 cm$^3$ round-bottomed flask, equipped with a magnetic stirrer and pressure equalising dropping funnel, was added butanol (55,6 g, 0.75 mol), triethylamine (55.7 g, 0.55 mol) and dichloromethane (300 cm$^3$). Methanesulfonyl chloride (57.3 g, 0.05 mol) was then added dropwise over a two-hour period from the dropping funnel, with cooling from an ice bath. The mixture was stirred for a further 24 hours at room temperature. The reaction mixture was filtered, concentrated on a rotary evaporator, and distilled (bp –80–90° C. at 5 mm Hg). This gave 68.1 g (98%) of a colourless oil.

Preparation of 1-butyl-3-methylimidazolium methanesulfonate ([bmim] [Oms])

In a 100 cm$^3$ round-bottomed flask, was added butyl methanesulfonate (15.3 g, 0.10 mol) and 1-methylimidazole (8.21 g, 0.10 mol). A reflux condenser was attached and the mixture heated at 100° C. for 48 hours. A vacuum was applied to the flask (1 mm Hg) to remove unreacted starting materials for 12 hours at 80° C. The low-melting salt [bmim] [Oms] (22.3 g, 95%) solidified on cooling.

References

1. J. S. Wilkes, J. A. Levisky, R. A. Wilson and C. L. Hussey, *Inorg. Chem.*, 1982, 21, 1263.
2. J. S., Wilkes and M. J. Zaworotko, *J. Chem. Soc., Chem. Commun.*, 1992, 965.
3. C. M. Gordon, J. Holbrey, A. R. Kennedy and K. R. Seddon, *J.Mater. Chem.*, 1998, 1, 2627; E. I. Cooper and E. J. M. O'Sullivan, in Molten Salts, Eds. R. J. Gale, G.

Blomgren and H. Kojima, The Electrochemical Society Proceedings Series, Pennington, N.J., 1992, 16, 386; P. Bonhote, A. P. Diaz, N. Papageorgiou, K. Kalanasundaram and M. Gratzel, *Inorg. Chem.*, 1996, 35, 1168; M. Fields, F. V. Hutson, K. R. Seddon and C. M. Gordon, World Patent, WO 98/06106, 1998.

4. A. A. K. Abdul-Sada, P. W. Ambler, P. K. G. Hodgson, K. R. Seddon and N. J. Stewart, World Patent, WO 95/21871, 1995.

5. Y. Chauvin, L. Mussmann and H. Olivier, *Angew. Chem. Int. Ed. Engl.*, 1995, 34, 2698; P. A. Z. Suarez, J. E. L. Dullius, S. Einloft, R. F. de Souza and J. Dupont, *Polyhedron*, 1996, 1217; A. L. Monteiro, F. K. Zinn, R. F. de Souza and J. Dupont, *Tetrahedron-Asymmetry*, 1997, 8, 177; P. A. Z. Suarez, J. E. L. Dullius, S. Einloft, R. F. de Souza and J. Dupont, *Inorg. Chim. Acta*, 1997, 255, 207.

6. C. J. Adams, M. J. Earle, G. Roberts and K. R. Seddon, *Chem. Commum.*, 1998, 2097; J. A. Boon, J. A. Levisky, J. L. Pflug and J. S. Wilkes, *J. Org. Chem.* 1986, 51, 480.

7. M. J. Earle, P. B. McCormac., and K. R. Seddon, *Green Chem.* 1999, 1, 23.

What is claimed is:

1. A process for preparing an ionic liquid or salt, wherein the cation of the ionic liquid or salt is an N-alkylated base, formed by reaction between an organic base and an alkylaring agent, wherein the organic base is selected from the group consisting of an imidazole, a substituted imidazole, a pyridine and a substituted pyridine and wherein the alkylating agent is a fluorinated ester or an alkyl sulfonate.

2. A process as claimed in claim 1 wherein the organic base is an imidazole or a substituted imidazole.

3. A process as claimed in claim 2 wherein the organic base is a 1-alkylimidazole.

4. A process as claimed in claim 3 wherein the organic base is a 1-methylimldazole.

5. A process as claimed in claim 1 wherein the organic base is a pyridine or a substituted pyridine.

6. A process as claimed in claim 5 wherein the organic base is an alkylpyridine.

7. A process as claimed in claim 1 wherein the reaction is carried out in the presence of a co-solvent.

8. A process as claimed in claim 7 wherein the co-solvent is acetonitrile.

9. A process as claimed in claim 1 wherein the reaction is carried out under pressure.

10. A process as claimed in claim 1 wherein the ionic liquid or salt comprises a trifluoroethanoate anion.

11. A process as claimed in claim 1 wherein the alkylating agent is ethyl trifluoroethanoate.

12. A process as claimed in claim 1 wherein the alkylaring agent is a methyl sulfonate.

13. A process as claimed in claim 12 wherein the alkylating agent is butyl methylsulfonate.

14. A process as claimed in claim 1 further comprising the step of reacting the ionic liquid or salt so formed with fluoroboric acid or hexafluorophosphoric acid.

* * * * *

UNITED STATES PATENT AND TRADEMARK OFFICE
CERTIFICATE OF CORRECTION

PATENT NO. : 6,774,240 B2
DATED : August 10, 2004
INVENTOR(S) : Seddon et al.

It is certified that error appears in the above-identified patent and that said Letters Patent is hereby corrected as shown below:

Column 5,
Line 25, "alkylaring" should be -- alkylating --

Signed and Sealed this

Seventh Day of June, 2005

JON W. DUDAS
*Director of the United States Patent and Trademark Office*